United States Patent
van den Broek et al.

[11] 3,944,576
[45] Mar. 16, 1976

[54] NOVEL STEROIDS OF THE OESTRANE SERIES SUBSTITUTED IN 7-POSITION

[75] Inventors: Albertus Joannes van den Broek; Jacob de Visser, both of Oss, Netherlands

[73] Assignee: Akzona Incorporated, Asheville, N.C.

[22] Filed: Mar. 27, 1974

[21] Appl. No.: 455,488

[30] Foreign Application Priority Data
Apr. 13, 1973  Netherlands.................. 7305171

[52] U.S. Cl.... 260/397.5; 260/239.55 C; 260/397.4
[51] Int. Cl.²............................................ C07J 1/00
[58] Field of Search.................. 260/397.4, 397.5

[56] References Cited
OTHER PUBLICATIONS
*Chemical Abstracts*, (74) 1971, p. 103, Pars. 29,176(a), Abstract of Frey et al. Publication.

*Primary Examiner*—Elbert L. Roberts
*Attorney, Agent, or Firm*—Francis W. Young; Philip M. Pippenger; Hugo E. Weisberger

[57] ABSTRACT

The invention relates to novel 7-substituted-steroids of the oestrane series of the general formula:

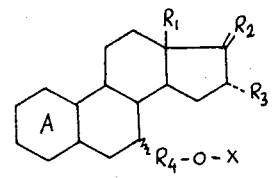

in which
ring A including carbon atom 6 is

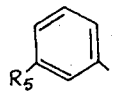 or 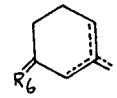

$R_1$ = an alkyl group with 1–4 C-atoms,
$R_2$ = oxygen or $(\alpha Y)(\beta Z)$, in which $Y$ = hydrogen or a saturated or unsaturated alkyl group with 1–4 C-atoms and $Z$ = a free, esterified or etherified hydroxyl group,
$R_3$ = hydrogen or a free or esterified hydroxyl group,
$R_4$ = an alkylene- or alkylidene group with 1–3 C-atoms,
$R_5$ = hydrogen or a free, esterified or etherified hydroxyl group,
$R_6$ = $H_2$, O, H(OH), H(Oalkyl) or H(Oacyl),
$X$ = H, an acyl group or an alkyl-, aralkyl-, cycloalkyl- or heterocyclic alkyl group, and
a double bond is present starting from carbon atom 5, and to processes for their preparation.

These novel steroids possess anabolic, androgenic, oestrogenic, progestative, ovulation-inhibiting and gonad-inhibiting properties.

5 Claims, No Drawings

NOVEL STEROIDS OF THE OESTRANE SERIES SUBSTITUTED IN 7-POSITION

The invention relates to novel steroids of the oestrane series substituted in 7-position and to processes for their preparation.

Steroids of the oestrane series alkylated in the 7-position are generally known, for example the 7α-methyloestrenes. The introduction of a 7α-methyl-group is generally attended with an increase of the biological activities. A novel group of steroids substituted in the 7-position and having surprisingly strong and valuable properties was prepared now.

The invention relates therefore to novel steroids with the general formula:

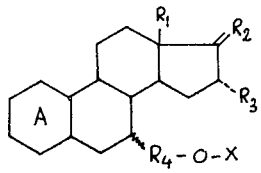

in which ring A including carbon atom 6 is

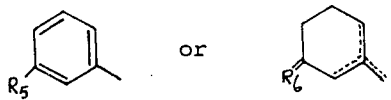

$R_1$ = an alkyl group with 1–4 C-atoms,
$R_2$ = oxygen or $(\alpha Y)(\beta Z)$, in which $Y$ = hydrogen or a saturated or unsaturated alkyl group with 1–4 C-atoms and $Z$ = a free, esterified or etherified hydroxyl group,
$R_3$ = hydrogen or a free or esterified hydroxyl group,
$R_4$ = an alkylene- or alkylidene group with 1–3 C-atoms,
$R_5$ = hydrogen or a free, esterified or etherified hydroxyl group,
$R_6$ = $H_2$, O, H(OH), H(Oalkyl) or H(Oacyl),
$X$ = H, an acyl group or an alkyl-, aralkyl-, cycloalkyl- or heterocyclic alkyl group, and
a double bond is present starting from carbon atom 5.

A special group is the group of novel steroids with the general formula:

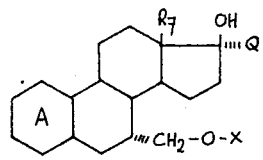

in which ring A is

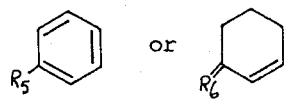

and X, $R_5$ and $R_6$ have the meanings given hereinbefore, $R_7$ is methyl or ethyl and Q is a saturated or unsaturated alkyl group with 1–4 C-atoms.

The compounds according to the invention appear to possess very valuable anabolic, androgenic, oestrogenic, progestative, ovulation-inhibiting and gonad-inhibiting properties. Especially, the 7α-methoxymethyl-17α-ethynyl-compounds according to the invention appear to have a very strong oestrogenic activity. The 17-oxo-compounds prepared in accordance with the invention are important intermediates for therapeutically valuable steroids.

The novel compounds can be prepared in various ways.

It is possible, for example, to start from a $\Delta^{4,6}$-oestradien-3-one and having Corey's reagent (dialkyl-sulphoxoniumalkylide, for example, dimethylsulphoxoniummethylide or diethylsulphoxoniummethylide) reacted with it. For this reaction the starting steroid should not carry other free oxo-groups, as interfering side reactions may occur then. A 3-oxo-$\Delta^4$-6,7-alkylidene-steroid comes into existence which by means of borontrifluoride-etherate in methanol is converted into the methylether of the corresponding $\Delta^4$-3-oxo-7-hydroxyalkyl-compound.

In this way it is possible, for example, to convert $\Delta^{4,6}$-17β-hydroxy-oestradien-3-one with dimethylsulphoxoniummethylide into $\Delta^4$-6,7-methylene-17β-hydroxy-oestren-3-one. A mixture of the 6α, 7α- and the 6β,7β-compound is formed then, which is separated in its components, for example by chromatography or by a repeated partial crystallisation. Thereupon the 6α,7α-methylene-compound is reacted with $BF_3$-etherate/methanol, during which reaction the $\Delta^4$-7α-methoxymethyl-17β-hydroxy-oestren-3-one is formed. It is also possible to have the isomeric mixture reacted with $BF_3$-etherate/methanol and thereafter separating, for example chromatographically, the formed mixture of the 7α-methoxymethyl- and 7β-methoxymethyl compound.

If in the case of the reaction with $BF_3$-etherate ethanol is taken instead of methanol, a 7-ethoxymethyl-oestrene is obtained.

If one starts from $\Delta^{4,6}$-oestradiene-3,17-dione, the 17-keto group is first protected by ketalisation, after which the 17-ketal is reacted with the dimethylsulphoxoniummethylide.

In the subsequent reaction with $BF_3$-etherate/alkanol, the 17-ketal-group is hydrolysed at the same time. A $\Delta^4$-7-alkoxymethyl-oestrene-3,17-dione is obtained.

If the diethylsulphoxoniummethylide is taken as Corey's reagent, a 7-(1'-alkoxy-)ethyl-group is obtained as substituent in the 7-position.

From the ether of the 7-hydroxyalkyl compounds the free hydroxylalkyl compound can be obtained by hydrolysis, for example by means of a strong acid, such as dinitrobenzenesulphonic acid or HI.

The 7α-hydroxymethyl-compounds according to the invention can also be obtained by having a $\Delta^{4,6}$-oestradien-3-one reacted with an alkalimetal cyanide, for example KCN, at a temperature between 35° C and 135° C in an inert solvent mixture, for example dimethylformamide/water. The cyanide is added to the 6–7 double bond, resulting in a $\Delta^4$-7α-cyano-oestren-3-one. By hydrolysis of the CN-group the corresponding 7α-carboxyl-compound is obtained. After protecting the 3-oxo-group in the form of the 3-ketal, the 7α-carboxyl-group can be reduced to the 7α-hydroxymethyl-group. It is also possible to reduce the 7α-CN-group to the 7α-aminomethyl-group, which by way of aminolysis can be converted into the 7α-hydroxymethyl-group.

The 7α-substituted compounds according to the invention can further be obtained by applying a 1,6-Grignard-reaction to a $\Delta^{4,6}$-oestradien-3-one. $\Delta^{4,6}$-17β-hydroxyoestradien-3-one, for example, is reacted with an alkoxyalkylmagnesiumchloride, for example methoxymethylmagnesiumchloride. As a reagent also lithiumdialkoxyalkylcopper can be applied, for example lithiumdimethoxyethylcopper. In this way a $\Delta^4$-7α-alkoxyalkyl-oestradien-3-one is obtained, for example a $\Delta^4$-7α-methoxymethyl-oestradien-3-one, from which, if desired, the corresponding 7α-hydroxyalkyl compound can be obtained by hydrolysis of the ether group.

Another alternative for preparing the 7-substituted compounds according to the invention exists therein that one starts from a 7-oxo-steroid of the oestrane-series or possibly a 7-hydroxy-steroid, the 7-hydroxy-group of which is oxidized first, and the 7-oxo-steroid is brought in reaction with a Wittig reagent being a phosphorane with the general formula:

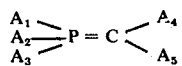

in which
$A_1$, $A_2$ and $A_3$ represent an alkyl- or arylgroup, for example, a methyl-, ethyl- or phenylgroup, $A_4$ is hydrogen, methyl, ethyl, an etherified or not etherified hydroxymethyl- or hydroxyethylgroup or an alkoxygroup, for example methoxy, or ethoxy, and $A_5$ is hydrogen, methyl or ethyl, with the understanding that the substituents $A_4$ and $A_5$ are chosen in such a way that in the finally obtained steroid the definition for $R_4$ is complied with. For preference triphenylphosphonium-alkylide-compounds are applied. Oxogroups present in the molecule elsewhere are temporarily protected against the effects of the Wittig reagent, for example, by ketalization.

The Wittig reagent is prepared by having a triaryl- or trialkylphosphine reacted with an alkyl- or alkoxyalkyl-halogenide in which case the corresponding triaryl (or trialkyl-) phosphonium (alkoxy) alkylhalogenide is produced. Under the influence of a base the last-mentioned compound can be converted into the desired triaryl- or trialkylphosphonium (alkoxy) alkylide.

As, however, the last-mentioned compounds are not stable and are easily converted or decomposed under the influence of air or moisture, such compounds are by preference allowed to be produced in situ. The reaction with the 7-oxo-steroid is usually performed therefore by adding a solution of the 7-oxo-steroid to a mixture of a trialkyl- or triarylphosphine and an (alkoxy) alkylhalogenide together with a suitable base, in the presence of a suitable organic solvent and excluding oxygen, for example in nitrogen atmosphere.

As (alkoxy) alkylhalogenide, is taken for example: methylchloride, ethylchloride, methoxymethylchloride, methoxyethylchloride, propylchloride, isopropylchloride.

As suitable bases can be mentioned alkalimetal compounds of aliphatic, aromatic or araliphatic hydrocarbons, for example butyllithium, phenyllithium or triphenylmethylsodium, alkylmagnesiumhalogenides, for example ethylmagnesiumbromide, alkalimetalamides, alkalimetalalcoholates and dimsylsodium (the reaction product of sodiumhydride and dimethylsulphoxide).

As solvents are applied dimethylsulphoxide, aliphatic ethers such as dimethylether, diethylether, dioxane or tetrahydrofuran and aromatic hydrocarbons, for example benzene or toluene.

After the reaction with the Wittig reagent an obtained 7-alkoxyalkylidene compound is hydrogenated for example in pyridine or ethylacetate with $H_2$/Pd on carbon or $H_2$/$PtO_2$ during which a mixture of the corresponding 7α- and 7β-alkoxyalkyl-derivatives is formed and an obtained 7-alkylidene-compound is converted into the 7-hydroxyalkyl-steroid by means of diborane during which likewise a mixture of the 7α- and 7β-derivatives is formed. The isomers can be separated, for example by way of chromatography and/or partial crystallization.

In this way, for example, $\Delta^{1,3,5(10)}$-3-hydroxy-oestratriene-7,17-dione-3-methylether-17-ketal can be converted with triphenyl-phosphoniummethoxymethylene into the corresponding 7-methoxy-methylene-compound, which by hydrogenation of the exocyclic double bond in the 7-position and hydrolysis of the ketal-group in the 17-position can be converted into $\Delta^{1,3,5(10)}$-3-hydroxy-7ξ-methoxymethyl-oestratrien-17-one-3-methylether. The same starting material can, by means of triphenylphosphoniummethylene, be converted into $\Delta$1,3,5(10)-3-hydroxy-7-methylene-oestratrien-17-one-3-methylether-17-ketal from which by means of diborane the $\Delta^{1,3,5(10)}$-3-hydroxy-7ξ-hydroxymethyl-oestratrien-17-one-3-methylether can be obtained. The mixtures of isomers are finally separated in the 7α- and 7β-derivatives.

After the introduction of a 7-substituent according to the invention, the substituents desired in the steroids elsewhere, in so far as not yet present, are introduced according to a method known per se. A possibly present hydroxyl-group in the 16-position is, for preference, already present in the starting steroids. A possibly present hydroxylgroup in the 7-substituent and/or in the 3,16 and/or 17-position can be esterified or etherified, if desired.

A present 3-oxo-$\Delta^4$-grouping can, if desired, be converted into a 3-hydroxy-A-aromatic-grouping, for example microbiologically with the aid of Arthrobacter simplex or chemically, for example by first converting the 3-oxo-$\Delta^4$-grouping in the enolacetate, brominating the enolacetate in the 6-position, for example by means of N-bromo-acetamide and treating the bromo derivative with an acid owing to which under splitting off of HBr the A-ring becomes aromatic.

The 3-oxo-$\Delta^4$-grouping can, if desired, following a method known per se, via a conversion into the 3-enolacylate, a reduction of the double bond between the carbon atoms 3 and 4 and hydrolysis of the 3-acylate, also be converted into a 3β-hydroxy-$\Delta^5$-grouping, after which, if desired, the 3β-hydroxy-group is esterified or etherified or is split off.

A present aromatic A-ring with a 3-methylether-group can, if desired, be converted into a 3-oxo-$\Delta^4$-grouping by way of the Birch-reduction method (reduction with an alkali metal in liquid $NH_3$) and conversion of the $\Delta^{2,5(10)}$-3-enolether by heating with a diluted strong acid. Hydrolysis of the $\Delta^{2,5(10)}$-3-enolether at room temperature with a weak acid, for example acetic acid, results in the 3-oxo-$\Delta^{5(10)}$-compound.

A present 3-oxo-or 3-hydroxy-group can, if desired, be split off for the preparation of the 3-desoxo-compounds.

The 3-oxo-group is converted for that purpose by reaction with a mercaptane or dithiol in the presence of $BF_3$, the etherate of it or $ZnCl_2$ into the thioketal group which is subsequently split off reductively, for example by treatment with an alkali metal, preferably lithium, in the presence of liquid ammonia or a lower aliphatic primary amine, such as methylamine or ethylamine.

A 3-hydroxy-group can be split off by converting same in the first place into a 3-halo- or 3-sulphonyloxy-group by halogenating with, for example, phosphorustrichloride or thionyl-chloride or sulphonylation with, for example, methanesulphonic acid, benzene-sulphonic acid, toluenesulphonic acid or the corresponding acid chlorides thereof, subsequently splitting off the 3-halo- or 3-sulphonyloxy-group reductively by treating with an alkali metal in liquid ammonia, a lower aliphatic amine, such as methylamine, or an alcohol, such as ethanol, or by treating with an alkali metal-aluminiumhydride, for example LiAlH$_4$.

The substituents desired in position 13 are preferably present already in the starting products. The 13$\beta$-alkyl-group can be a methyl-, ethyl-, propyl-, isopropyl-, butyl- or isobutylgroup.

The substituents desired in position 17 can be present already in the starting products, In so far as not yet present, they can be introduced, if desired, as yet, according to a method known per se.

A present 17-hydroxygroup can be oxidized to a 17-oxo-group, for example by way of the Oppenauer method or by means of chromiumtrioxide. A present 17-oxo-group can be reduced, if desired, to a 17-hydroxygroup, for example by reduction with NaBH$_4$ in alkaline methanol.

The introduction of a saturated or unsaturated alkyl-group in position 17 is performed by having the 17-oxosteroid reacted with a metal-derivative of a saturated or unsaturated, substituted or unsubstituted, aliphatic hydrocarbon, followed if necessary by a reduction of the thus introduced side-chain.

The metal-derivative can be a Grignard-compound, for example the magnesium bromide of the hydrocarbon concerned or an alkyllithium-compound. A special way of performance of the condensation reaction for the preparation of the 17$\beta$-hydroxy-17$\alpha$-alkynyl-compounds consists in that the 17-oxo-steroid is reacted with a triple unsaturated hydrocarbon in the presence of an alkali metal or an alkali metal compound, such as an alkalimetal amide or alcoholate, or with a metal compound of a triple unsaturated hydrocarbon, such as an alkalimetal- or earthalkalimetal-compound.

The 17-alkylation can also be performed in two phases, by preparing first, by way of a condensation-reaction, the 17$\beta$-hydroxy-17$\alpha$alkynyl-compound and converting same by reduction, for example with the aid of hydrogen in the presence of a catalyst, such as nickel or Pd/BaSO$_4$, into the corresponding 17$\alpha$-alkenyl- or 17$\alpha$-alkyl-compound.

The hydrocarbon radical possibly present in the final products in position 17 can be, for example, a methyl-, propyl-, butyl-, isopropyl-, vinyl-, propenyl-, isopropenyl-, allyl-, methallyl-, ethynyl-, propynyl-, propargyl-, butynyl-, butadienyl-, butadiynyl-, propadienyl- or butenynyl-radical.

The estergroup possibly present in the final products in the positions 3, 16 and/or 17 and/or in the 7-substituent may be derived from an anorganic acid, such as phosphoric acid or from a saturated or unsaturated organic carboxylic acid with 1–18 carbon atoms. The conversion of a hydroxygroup into an estergroup can be performed according to a method known per se, for example by reacting the hydroxysteroid with the acid concerned or a functional derivative of it, such as the anhydride or the halogenide. The esterification of the 17$\beta$-hydroxy-group, which is formed during the 17-alkylation, can also be performed by having the reaction product of the condensation of the 17-oxo-steroids with a metal derivative of an unsaturated hydrocarbon radical, without a preceding hydrolysis, reacted with the corresponding acid or a functional derivative of it. The esterification can, for example, also be performed by having the steroid reacted with a carboxylic acid anhydride, such as acetic acid anhydride in the presence of 4-dimethylamino-pyridine, preferably at the same time in the presence of a tertiary amine, such as trimethylamine.

As examples of the organic carboxylic acids to be applied in the esterification are mentioned: formic acid, acetic acid, propionic acid, butyric acid, valeric acid, capric acid, undecylic acid, lauric acid, tridecylic acid, myristic acid, pentadecylic acid, oleic acid, palmitic acid, stearic acid, adamantane carboxylic acid, trimethyl-acetic acid, diethylacetic acid, cyclohexane carboxylic acid, cyclopentylpropionic acid, cyclohexylbutyric acid, cyclohexylpropionic acid, undecylenic acid, benzoic acid, phenyl acetic acid, phenylpropionic acid, phenyl butyric acid, malonic acid, succinic acid, glutaric acid, pimelinic acid and tartaric acid. As said, also functional derivatives of same can be applied, such as the anhydrides or acid chlorides.

The ether groups present in the final products in the positions 3 and/or 17 and/or in the 17-substituent can be derived from an aliphatic, aromatic, araliphatic or heterocyclic hydrocarbon. Examples of such ether groups are the methylether-, ethylether-, butylether-, cyclopentylether-, tetrahydropyranylether-, cyclohexylether- and vinylethylether groups.

The esterification of a hydroxyl group can be performed according to standard methods. The hydroxy group possibly present in the 7-substituent can, for example, be converted into the methoxy group by means of diazomethane in ether or methanol in the presence of fluoroboric acid or BF$_3$-etherate. An alkoxy group can also be formed by having the hydroxy group reacted with an alkyliodide, for example methyliodide or ethyliodide, in the presence of silveroxide or silvercarbonate or in the presence of sodiumhydride in dimethylsulphoxide.

A partial etherification, that is to say the etherification of, for example, the 17$\beta$-group, during which the etherification of a present 3-hydroxy-group is not wanted, can be performed by temporarily protecting, in a suitable way, the hydroxy group that is not to be etherified. Thus the 17$\beta$-hydroxy group in the presence of a 3-hydroxy-A-aromatic-group can be converted into the tetrahydropyranylgroup by protecting the 3-hydroxy group in the form of a benzoate of it and removing the benzoate group in position 3 after the introduction of the ether group in position 17.

The compound obtained by the process of the invention can be administered parenterally or orally in the form of suspensions, emulsions, or solid pharmaceutical dosage units, such as tablets, pills or coated tablets, usually after being mixed with auxiliaries and, if required, other active components.

The invention is illustrated by the following examples:

EXAMPLE I

A solution of 30 gm of $\Delta^{4,6}$-oestradiene-3,17-dione in 1200 ml of benzene and 60 ml of ethylene glycol were refluxed in the presence of 0.6 g. of p-toluene sulphonic acid under separation of water for 1 hour. After cooling down to 20° C, 6 ml of pyridine were added and after that the reaction mixture was washed to neutral with a 5% sodium hydrogen carbonate solution and water. The organic phase was evaporated and crystallized from acetonitril, by which 23 grams of $\Delta^{4,6}$-oestradiene-3,17-dione 17-ethylene-ketal were obtained with a melting point of 133°–136°C and $[\alpha]_D^{20} = -57°$ (chloroform).

b. To the dimethylsulphoxoniummethylide-reagent, obtained by having 22 gm. of trimethylsulphoxoniumiodide in 670 ml of dimethylsulphoxide reacted with 4.8 grams NaH (50% oil-suspension) for 20 minutes at room temperature, 23 gm of $\Delta^{4,6}$-oestradiene-3,17-dione 17-ethyleneketal were added. After 15 hours' stirring at room temperature, the reaction mixture was poured out into water and the resulting precipitate was filtered off. Chromatography of the reaction product over silicagel and elution with benzene/ethylacetate (8:2) resulted in 13.8 gm of the isomermixture $6\xi,7\xi$-methylene-$\Delta^4$-oestrene-3,17-dione 17-ethyleneketal in a ratio of $6\alpha,7\alpha$-methylene- and $6\beta,7\beta$-methylene-compound of 3:1.

c. A solution of 13.8 gm of $6\xi,7\xi$-methylene-$\Delta^4$-oestrene-3,17-dione 17-ethyleneketal in 138 ml of 70% acetic acid was stirred for 1 hour at 50°C and poured out after that in 1500 ml of ice water. Extraction by means of methylene chloride and washing with water to neutral resulted in 10.8 gm of $6\xi,7\xi$-methylene-$\Delta^4$-oestrene-3,17-dione.

d. To a solution of 10.8 gm of $6\xi,7\xi$-methylene-$\Delta^4$-oestrene-3,17-dione in 165 ml of methanol were added 1.5 ml of $BF_3$-etherate after which the reaction mixture was boiled for 1 hour. After pouring out into water the reaction mixture was extracted by means of methylene chloride, washed to neutral and evaporated. The crude product was chromatographed over silicagel and crystallized from acetonitril to obtain: 2.5 gm of $7\alpha$-methoxymethyl-$\Delta^4$-oestrene-3,17-dione with a melting point of 178°–180°C and $[\alpha]_D^{20} = +109°$ (chloroform). By repeated crystallizations 0.6 gm of $7\beta$-methoxymethyl-$\Delta^4$-oestrene-3,17-dione with a melting point of 151°–152° C was obtained. From the 7-methoxymethyl compounds the corresponding 7-hydroxymethyl compounds were obtained by hydrolysis of the ethergroup with the aid of $BF_3$-etherate and acetic acid anhydride.

e. In the same manner as described in (a) up to and inclusive (d) $\Delta^{4,6}$-oestradiene-3,17-dione was converted with diethylsulphoxoniumethylide and $BF_3$-etherate/methanol into $7\alpha$-(1'-methoxy-)ethyl-$\Delta^4$-oestrene-3,17-dione and the corresponding $7\beta$-compound, from which by means of hydrolysis of the ethergroup the corresponding $7\alpha$- and $7\beta$-(1'-hydroxy)-ethyl-compounds were obtained.

EXAMPLE II a. To a suspension of 3.5 gm of $7\alpha$-methoxymethyl-$\Delta^4$-oestrene-3,17-dione in 35 ml of methanol and 3.5 ml of ethanedithiol were added 3.5 ml of $BF_3$-etherate at 0°C. After stirring the mixture at this temperature for 1 hour the precipitate formed was filtered off, washed with cold methanol and dried. In this way 3.3 g. of $7\alpha$-methoxymethyl-$\Delta^4$-oestrene-3,17-dione 3-ethylenedithioketal were obtained with a melting point of 174°–176°C and $[\alpha]_D^{20} = +122°$ (chloroform).

b. A suspension of 3.3 gm of $7\alpha$-methoxymethyl-$\Delta^4$-oestrene-3,17-dione 3-ethylenedithioketal, 0.5 gm $NaBH_4$ and 132 ml of ethanol were stirred in a $N_2$-atmosphere at 5°–12°C for 2 hours. After that the reaction mixture was neutralized with 2 ml of 50% acetic acid and diluted with water. The precipitate was filtered off. In this way 3.3 gm of crude $7\alpha$-methoxymethyl-$7\beta$-hydroxy-$\Delta^4$-oestren-3-one 3-ethylenedithioketal were obtained.

c. A solution of 3.3 gm of crude $7\alpha$-methoxymethyl-$17\beta$-hydroxy-$\Delta^4$-oestren-3-one 3-ethylenedithioketal in 15 ml of tetrahydrofuran were added to a solution of 1.4 gm of sodium in 50 ml of liquid ammonia at $-40°$ C. After 30 minutes' stirring the excess of sodium was destroyed and the reaction mixture worked up by extraction. Crystallization from acetonitril resulted in 2.0 gm of $7\alpha$-methoxymethyl-$\Delta^4$-oestren-$17\beta$-ol with a melting point of 135°–138°C and $[\alpha]_D^{20} = +14°$ (chloroform). In the same way $7\beta$-methoxymethyl-$\Delta^4$-oestren-$17\beta$-ol was obtained by starting from $7\beta$-methoxymethyl-$\Delta^4$-oestrene 3,17-dione. From the $17\beta$-hydroxy-compounds obtained the $17\beta$-esters derived from acetic acid and phenylpropionic acid, were prepared.

EXAMPLE III

To a solution of 2.0 gm of $7\alpha$-methoxymethyl-$\Delta^4$-oestren-$17\beta$-ol in 115 ml of acetone, 2.0 ml of 8 N $CrO_3$ were added dropwise in 15 minutes at a temperature of $-10°$C. After stirring for 15 minutes and working up of the product precipitated in water, by filtration, 1.4 gm of $7\alpha$-methoxymethyl-$\Delta^4$-oestren-17-one with a melting point of 148°–150°C and $[\alpha]_D^{20} = +93°$ (chloroform) were obtained by way of crystallization from acetone.

In the same way $7\beta$-methoxymethyl-$\Delta^4$-oestren-17-one was obtained as an oil by starting from the corresponding $17\beta$-hydroxy-compound.

EXAMPLE IV

A solution of 1.5 gm of $7\alpha$-methoxymethyl-$\Delta^4$-oestren-17-one in 5 ml of dry tetrahydrofuran were added to a potassium acetylide-suspension in 25 ml of tetrahydrofuran. After reacting for 45 minutes at 0°–5°C the reaction mixture was worked up by extraction and chromatography over silicagel. Crystallization from pentane gave 1.0 gm of $7\alpha$-methoxymethyl-$17\alpha$-ethinyl-$\Delta^4$-oestren-$17\beta$-ol with a melting point of 71°–73°C and $[\alpha]_D^{20} = +68°$ (chloroform).

In the same way $7\beta$-methoxymethyl-$17\alpha$-ethinyl-$\Delta^4$-oestren-$17\beta$-ol was obtained as an oil, starting from $7\beta$-methoxymethyl-$\Delta^4$-oestren-17-one.

By esterification the obtained $17\beta$-hydroxy-compounds were converted into the $17\beta$-acylates, derived from acetic acid, valeric acid, lauric acid and phenylpropionic acid.

EXAMPLE V

A solution of 2 gm of $7\alpha$-methoxymethyl-$\Delta^4$-oestrene-3,17- dione in 20 ml of acetic acid anhydride, 10 ml of acetylchloride and 1 ml of pyridine were refluxed for 3 hours. After cooling down to room temperature the reaction mixture was poured out into water and the precipitate was filtered off. After drying in vacuum the crude 3-hydroxy-7α-methoxymethyl-$\Delta^{3,5}$-estradien-17-one 3-acetate was dissolved in 100 ml of t-butanol and 16 ml of water. To this solution was added portionwise 0.9 gm of N-bromoacetamido for 5 minutes. After 15 minutes' stirring the excess of N-bromo-acetamide is removed by adding an aqueous sodium bisulphite-solution. After working up by extraction the residue was heated on a waterbath until the HBr-development came to a stop.

Chromatography and crystallization from acetone gave 1.2 gm of 3-hydroxy-7α-methoxymethyl-$\Delta^{1,3,5}$-oestradien-17-on, melting point 179°–180°C, $[\alpha]_D^{20} = +123°$ (in $CHCl_3$).

Example VI

To a suspension of potassium acetylide, prepared from 3.8 gm of potassium-t-butylate in 30 ml of tetrahydrofuran and acetylene, 0.9 gm of 3-hydroxy-7α-methoxymethyl-$\Delta^{1,3,5(10)}$-oestratrien-17-one in 5 ml of tetrahydrofuran was added. After a 2 hours' reaction at 0°–5°C the reaction mixture was worked up by pouring out into water and filtering off of the precipitate. By crystallization from di-isopropylether, 0.6 gm of 7α-methoxymethyl-17α-ethinyl-$\Delta^{1,3,5(10)}$-oestratriene-3,17β-diol were obtained with a melting point of 177°–178°C and $[\alpha]_D^{20} = -6°$ (in $CHCl_3$).

EXAMPLE VII

To a solution of 0.9 gm of 3-hydroxy-7α-methoxymethyl-$\Delta^{1,3,5(10)}$-oestratrien-17-on in 18 ml of methanol were added consecutively at −5° C a solution of 0.18 gm of NaOH in 1.8 ml of water and 0.3 gm of $NaBH_4$. After 1.5 hours' stirring at 0° C the reaction mixture was poured out and filtered off. In this way 0.9 gm of 7α-methoxymethyl-$\Delta^{1,3,5(10)}$-oestratriene-3,17β-diol, with a melting point of 202°–203° C and $[\alpha]_D^{20} = +38°$ (in $CHCl_3$), were obtained.

EXAMPLE VIII a. To a solution of 0.9 gm of 7α-methoxymethyl-$\Delta^{1,3,5(10)}$oestratriene-3,17β-diol in 3.5 ml of acetone were added a solution of 1.4 gm of NaOH in 18 ml of water after which 0.9 ml of benzoylchloride were added dropwise at 40°C. After working up by means of extraction and chromatography 1.0 gm of 7α-methoxymethyl-$\Delta^{1,3,5(10)}$-oestratriene-3,17β-diol 3-benzoate was obtained.

b. A solution of 1.0 gm of 7α-methoxymethyl-$\Delta^{1,3,5(10)}$-oestratriene-3,17β-diol 3-benzoate in 17 ml of tetrahydrofuran and 3.2 ml of dihydropyran were stirred for 1 hour with 25 mg of paratoluenesulphonic acid at room temperature. The reaction mixture was worked up by extraction. In this way a residue of 1.1 gm of 7α-methoxymethyl-$\Delta^{1,3,5(10)}$-oestratriene-3,17β-diol 3-benzoate 17-pyranylether were obtained.

c. A suspension of 1.1 gm of 7α-methoxymethyl-$\Delta^{1,3,5(10)}$-oestratriene-3,17β-diol 3-benzoate 17-pyranylether in 100 ml of methanol was stirred for 2 hours with 0.2 gm of NaOH in 0.5 ml of water at room temperature. After that the reaction mixture was acidified with 50% acetic acid, extracted with methylenechloride and washed to neutral. After evaporating in vacuo the residue was gaschromatographed over silicagel and the purified fractions were collected. In this way 0.9 gm of 7α-methoxymethyl-$\Delta^{1,3,5(10)}$-oestratriene-3,17-diol 17β-pyranylether as a mixture of the 2-pyranylether isomers with $[\alpha]_D^{20} = +29°$ (chloroform) were obtained.

EXAMPLE IX a. To a solution of 1.32 gm of 17β-hydroxy-$\Delta^{4,6}$-oestradien-3-one 17-acetate in 18 ml of dimethylformamide and 1.8 ml of water were added 0.54 gm of KCN and 0.32 gm of $NH_4Cl$. The mixture was stirred for 3 hours at a temperature of 85°C and in a $N_2$-atmosphere, after that poured out into ice water and extracted with ethylacetate. The extract was washed with water to neutral. After drying on sodium sulphate the solvent was distilled of in vacuo after which the crude product was crystallized from diethylether. The result was that 7α-cyano-17β-hydroxy-$\Delta^4$-oestren-3-one 17-acetate with a melting point of 195°–198°C was obtained.

b. To a solution of 4.8 gm of 7α-cyano-17β-hydroxy-$\Delta^4$-oestren-3-one 17-acetate in 130 ml of methanol a solution of 0.9 gm of potassium carbonate in 20 ml of methanol was added, after which the mixture was stirred for 1 hour, under reflux and in nitrogen atmosphere. The mixture was cooled down after that, acidified by means of acetic acid to pH 6.5 and then diluted with ice water. The crystals of 7α-cyano-17β-hydroxy-$\Delta^4$-oestren-3-one obtained were filtered off, washed with water to neutral and after that dried in vacuo.

c. To a solution of 1.29 gm of 7α-cyano-17β-hydroxy-$\Delta^4$-oestren-3-one in 15 ml of benzene, 1.4 ml of ethanediol, 2 ml of ethylorthoformiate and 3.0 mg of para-toluenesulphonic acid were added, after which the reaction mixture was stirred at room temperature in nitrogen atmosphere for 1¼ hour. After pouring out into ice water neutralisation was effected by means of a $NaHCO_3$-solution and then extracted with methylene chloride, after which the extract was washed with water to neutral and dried on sodiumsulphate. After distillation of the solvent in vacuo, 3,3-ethylenedioxy-7α-cyano-$\Delta^5$-oestren-17β-ol was obtained.

d. To a solution of 4.7 gm of 3,3-ethylenedioxy-7α-cyano-$\Delta^5$-oestren-17β-ol in 18 ml of dry tetrahydrofuran and 18 ml of 2,3-dihydropyran, 0.15 ml of $POCl_3$ was added, after which the mixture was stirred at room temperature for 3 hours under exclusion of moisture. The mixture was poured out into water, and after that extracted with methylene chloride. The extract was washed with water to neutral and dried on sodium-sulphate. Distillation of the solvent in vacuo gave the 17β-pyranylether of 3,3-ethylenedioxy-7α-cyano-$\Delta^5$-oestren-17β-ol.

e. To a solution of 2.9 gm of 3,3-ethylenedioxy-7α-cyano-$\Delta^5$-oestren-17β-ol 17β-pyranylether in 80 ml of ethyleneglycol were added a solution of 5 gm of KOH in 20 ml of water, after which the mixture was stirred for 24 hours in a nitrogen atmosphere and at reflux temperature. The reaction mixture was cooled down, poured out into ice water and acidified with diluted sulphuric acid. The crystals of the thus obtained 3,3-ethylenedioxy-17β-hydroxy-$\Delta^5$-oestrene-7α-carboxylic acid 17β-pyranylether were filtered off, washed with water and dried in vacuo at room temperature.

f. To a suspension of 4 gm of $LiAlH_4$ in 100 ml of dry benzene was added a solution of 3,3 gm of 3,3- ethylenedioxy-17β-hydroxy-Δ$^5$-oestrene-7α-carboxylic acid-17β-pyranylether in 100 ml of dry benzene, after which the reaction mixture was stirred for 4.5 hours at reflux temperature. The mixture was cooled after that and the excess of LiAlH$_4$ was decomposed with ethylacetate. The mixture was diluted then with water and extracted with benzene. The benzene extracts were washed with water to neutral. After drying on sodiumsulphate the solvent was distilled off in vacuo, resulting in 3,3-ethylenedioxy-7α-hydroxymethyl-Δ$^5$-oestren-17β-ol-17β-pyranylether, from which by hydrolysis in acetone with hydrochloric acid 7α-hydroxymethyl-17β-hydroxy-Δ$^4$-oestren-3-on was released.

EXAMPLE X a. A mixture of 0.96 gm NaH (50% suspension in oil) in 18 ml of dimethylsulphoxide was stirred in a nitrogen atmosphere for 1.5 hour at a temperature of +75°C and subsequently cooled down to room temperature. After that a solution of 4.3 gm of 3,3-ethylenedioxy-7α-hydroxymethyl-Δ$^5$-oestren-17β-ol 17-pyranylether in 40 ml of dimethylsulphoxide was added stirring the mixture in a nitrogen atmosphere at room temperature for 0.5 hour. After adding 3.7 ml of methyliodide the reaction mixture was stirred for another 3 hours at room temperature. The mixture was poured out into ice water and extracted with methylenechloride after which the extract was washed with water to neutral. After drying the extract on sodiumsulphate the solvent was distilled off in vacuo, resulting in 3,3-ethylenedioxy-7α-methoxymethyl-Δ$^5$-oestren-17β-ol 17β-pyranylether.

b. To a solution of 6.9 gm of 3,3-ethylenedioxy-7α-methoxymethyl-Δ$^5$-oestren-17β-ol 17β-pyranylether in 200 ml of acetone were added 10 ml of 2,3 N hydrochloric acid, after which the mixture was stirred in a nitrogen atmosphere for 1¾ hour. The mixture was poured out into ice water. The crystals of the thus obtained 7α-methoxymethyl-17β-hydroxy-Δ$^4$-oestren-3-on were filtered off, washed with water to neutral and dried in vacuo.

EXAMPLE XI a. In a nitrogen atmosphere 1.73 gm of NaH (50% suspension in oil) was added to 17 ml of dimethylsulphoxide. The mixture was stirred at 75°C for one hour and cooled down afterwards to 0°C. Under nitrogen a solution of 12.8 gm of methyltriphenylphosphoniumbromide in 36 ml of dimethylsulphoxide were added to the mixture. The thus obtained mixture was stirred at room temperature for 15 minutes, after which a solution of 4.0 gm of 3-hydroxy-Δ$^{1,3,5(10)}$-oestratriene-7,17-dion-3-methylether-17,17-ethyleneketal in 60 ml of tetrahydrofuran were added during a period of 10 minutes. The reaction mixture was stirred for 4 hours at 50°C. After cooling the mixture was poured out into water and extracted with ether. The ether-extract was evaporated in vacuo and the residue was chromatographed over a column of silicagel, during which 3-hydroxy-7,7-methylene-Δ$^{1,3,5(10)}$-oestratrien-17-on-3-methylether-17,17-ethyleneketal was isolated.

b. To a solution of 0.8 gm of LiAlH$_4$ in 70 ml of ether was added at 5°C a solution of 2 gm of 3-hydroxy-7,7-methylene-Δ$^{1,3,5(10)}$-oestratrien-17-on-3-methylether-17,17-ethyleneketal in 40 ml of ether and 3.6 ml of BF$_3$-etherate. The reaction mixture was stirred for 2 hours at 0°C, after which the excess of hydride was destroyed by means of acetone. The precipitate was filtered off and the mother-liquor was evaporated to dryness. The residue was dissolved in 70 ml of tetrahydrofuran. To this solution was added at 0°C a solution of 9.4 gm of KOH in 96 ml of water and 54 ml of a 30% hydrogen peroxide-solution. After stirring for 1 hour at 0°C the reaction mixture was poured out into water. Extraction with ether and evaporation of the extract gave a residue from which by way of chromatography over a silicacolumn, 1.1 gm of 3-hydroxy-7α-hydroxymethyl-Δ$^{1,3,5(10)}$-oestratrien-17-one-3-methylether-17,17-ethyleneketal and 0.5 gm of the corresponding 7β-hydroxymethyl compound were isolated.

c. 1 gm of 3-hydroxy-7α-hydroxymethyl-Δ$^{1,3,5(10)}$-oestratrien-17-one-3-methylether-17,17-ethyleneketal was dissolved in 10 ml of acetone. To the solution 0.1 gm of p-toluenesulphonic acid was added. The reaction-mixture was stirred for 16 hours at room temperature. After the addition of a saturated NaHCO$_3$-solution the reaction-mixture was poured out into ice water. The precipitate was filtered off, washed with water and dried in vacuo. After crystallization 0.8 gm of 3-hydroxy-7α-hydroxy-methyl-Δ$^{1,3,5(10)}$-oestratrien-17-one-3-methylether was obtained. From the 17,17-ethyleneketal of the corresponding 7β-hydroxymethyl compound, the 3-hydroxy-7β-hydroxymethyl-Δ$^{1,3,5(10)}$-oestratrien-17-one-3-methylether was obtained in a similar way. By esterification the corresponding 7α- and 7β-acyloxymethyl compounds were obtained, derived from acetic acid, propionic acid, capric acid, phenylpropionic acid, undecylenic acid and succinic acid.

EXAMPLE XII a. A mixture of 6.6 gm of triphenylphosphine and 2.1 gm of methoxymethylchloride in 160 ml of ether were refluxed for 52 hours. After being cooled the solution was filtered and the extract was re-crystallized from chloroform/ethylacetate, resulting in 6.7 gm of methoxymethyltriphenylphosphoniumchloride.

b. 6.7 gm of methoxymethyltriphenylphosphoniumchloride were suspended in 80 ml of tetrahydrofuran. When stirring and in a nitrogen atmosphere 20 ml of n-butyllithium were added dropwise in 15 minutes. The brownreddish solution was stirred for 2 hours. To this solution was added at room temperature when stirring and in a nitrogen atmosphere a solution of 1.1 gm of 3-hydroxy-Δ$^{1,3,5(10)}$-oestratriene-7,17-dione-3-methylether-17,17-ethyleneketal in 30 ml of tetrahydrofuran. After that the reaction mixture was refluxed for 6 hours. After cooling the precipitate was sucked off and washed with a tetrahydrofuran-ether mixture. The filtrate was poured out into water and extracted with a tetrahydrofuran-ether mixture. The collected tetrahydrofuran-ether mixtures were evaporated in vacuo. From the residue 3-hydroxy-7,7-methoxymethylene-Δ$^{1,3,5(10)}$-oestratrien-17-one-3-methylether-17,17-ethylene-ketal was isolated by chromatography over a silica column.

c. 1 gm of 3-hydroxy-7,7-methoxymethylene-$\Delta^{1,3,5(10)}$-oestratrien-17-one-3-methylether-17,17-ethyleneketal in 60 ml of ethanol was hydrogenated with $H_2$ with the aid of 0.25 gm of $PtO_2$ as catalyst. After the reaction the mixture is filtrated over hyflo. The filtrate was evaporated in vacuo. From the residue 3-hydroxy-7$\alpha$-methoxymethyl-$\Delta^{1,3,5(10)}$-oestratrien-17-one-3-methylether-17,17-ethyleneketal and the corresponding 7$\beta$-methoxymethyl-compound was isolated by way of chromatography over a silicacolumn. In the way as described in Example XI (c) the corresponding 17-ketones were set free from the 17-ketals.

EXAMPLE XIII a. A solution of 0.5 ml of sulphuric acid in 25 ml of isopropenyl acetate was added to a solution of 19.3 g of 3-hydroxy-7$\alpha$-methoxymethyl-$\Delta^{1,3,5(10)}$-oestratrien-17-one in 290 ml of isopropenyl acetate. The mixture was heated for 5 hours while distilling off 140 ml of isopropenyl acetate. After cooling 30 g of sodium acetate was added and the mixture was evaporated to dryness in vacuo. After stirring with some water the residue was extracted with ether. The combined ether-layers were washed neutral, dried and evaporated to dryness. The residue was chromatographed on silicagel yielding 15.9 g of 7$\alpha$-methoxymethyl-$\Delta^{1,3,5(10),16}$-oestratetraene-3,17-diol diacetate (m.p. 131°–132°C).

b. 15.9 g of the diacetate obtained under (a) were dissolved in 80 ml of ethyl acetate. To this solution 70 ml of a solution of monoperphtalic acid (0.94 M) were added. After putting aside for 1.5 hours at room temperature the solution was washed with 1 N NaOH-solution and then washed with water till neutral. Drying and evaporation of the solution yielded a residue of 16.0 g. of 7$\alpha$-methoxymethyl-16$\alpha$,17$\alpha$-epoxy-$\Delta^{1,3,5(10)}$-oestratriene-3,17$\beta$-diol diacetate (m.p. 143°–145°C).

c. 16.0 g of the epoxy-compound, obtained under (b) was dissolved in 140 ml of methanol. To this solution a solution of 5.5 g of NaOH in 11 ml of water and 70 ml of methanol was added. After stirring for 10 minutes at 40°C the mixture was cooled down to −10°C, whereafter 1.5 g of sodiumboronhydride were added. Stirring at −10°C for 1.5 hours was followed by stirring at +30°C for ½ hour, whereafter the reaction mixture was diluted with water and neutralized with acetic acid (50%). Extraction with ethyl acetate, neutralization of the combined organic layers, drying and evaporation to dryness in vacuo yielded 13.0 g crude 7$\alpha$-methoxymethyl-$\Delta^{1,3,5(10)}$-oestratriene-3,16$\alpha$,17$\beta$-triol (amorphous).

d. 13.0 g of the crude product obtained under (c) was dissolved in 32 ml of dimethylformamide and 32 ml of acetetone. After adding 240 mg of p-toluene sulphonic acid hydrate the solution was refluxed for 15 minutes. After cooling the solution was diluted with water and extracted with ethyl acetate. The combined organic layers were washed till neutral, dried and evaporated to dryness in vacuo. The residue was chromatographed on silicagel. Crystallization from ethyl/ethanol (96%) gave 2.4 g of 7$\alpha$-methoxymethyl-$\Delta^{1,3,5(10)}$-oestratriene-3,16$\alpha$,17$\beta$-triol. ½ $H_2O$ (m.p. 161°C with decomposition, $[\alpha]_D^{20} = -33°$ in pyridine).

EXAMPLE XIV

A solution of 1.0 g of 7$\alpha$-methoxymethyl-$\Delta^{1,3,5(10)}$-oestratriene-3,16$\alpha$,17$\beta$-triol in 20 ml pyridine, to which 6.0 g succinic acid anhydride was added, was heated at 70°C in a nitrogen atmosphere for 16 hours. After the addition of 40 ml of water the mixture was heated at 50°–55°C for another 3 hours, then cooled down to 2°C and diluted with 110 ml of 2N sulphuric acid.

The mixture was extracted with ether and the combined ether-layers were washed to remove sulphate, dried, treated with decolorisation carbon and evaporated to dryness in vacuo. Chromatography of the residue on silicagel yielded 1.4 g 7$\alpha$-methoxymethyl-$\Delta^{1,3,5(10)}$-oestratriene-3,16$\alpha$,17$\beta$-triol 16$\alpha$,17$\beta$-dihemisuccinate (amorphous, $[\alpha]_D^{20} = -39°$ in pyridine).

EXAMPLE XV

A solution of 2.0 g of 3-hydroxy-7$\alpha$-methoxymethyl-$\Delta^{1,3,5(10)}$-oestratrien-17-one in 20 ml of dry ether was added to 75 ml acetic acid anhydride. After cooling to 0°C 9 ml of fresh distilled borontrifluoride-etherate were added. The mixture was kept at 0°C for 12 hours and was then poured out into ice-water. After 2 hours the mixture was extracted with ether. The combined ether-layers were washed with water containing some sodiumbicarbonate, dried and evaporated to dryness, yielding a residue of 1.95 g.

Chromatography of the residue and crystallization from ether gave 3-hydroxy-7$\alpha$-hydroxymethyl-$\Delta^{1,3,5(10)}$-oestratrien-17-one diacetate (m.p. 114°–116°C, $[\alpha]_D^{20} = +74°$ in $CHCl_3$).

EXAMPLE XVI

To a solution of 1.0 g of 3-hydroxy-7$\alpha$-hydroxymethyl-$\Delta^{1,3,5(10)}$-oestratrien-17-one diacetate in 30 ml of methanol 1.2 g of KOH in 6 ml of water were added. The mixture was put aside for 16 hours, poured out into water and further processed by extraction and evaporation of the extract to dryness.

The residue was treated with potassiumacetylide as described in Example VI. Crystallization of the reaction-product from acetonitril gave 0.7 g of 7$\alpha$-hydroxymethyl-17$\alpha$-ethynyl-$\Delta^{1,3,5(10)}$-oestratriene-3,17$\beta$-diol (m.p. 118°–120°C, $[\alpha]_D^{20} = -2°$ in $CHCl_3$).

What is claimed is:

1. A 7-substituted steroid of the oestrane series, selected from the group consisting of 7$\alpha$-methoxymethyl-17$\alpha$-ethynyl-$\Delta^4$-oestren-17$\beta$-ol, 7$\alpha$-methoxymethyl-17$\alpha$-ethynyl-$\Delta^{1,3,5(10)}$-oestratriene-3,17$\beta$-diol, 7$\alpha$-hydroxymethyl-17$\alpha$-ethynyl-$\Delta^{1,3,5(10)}$-oestratriene-3,17$\beta$-diol, and 7$\alpha$-methoxymethyl-$\Delta^{1,3,5(10)}$-oestratriene-3,16$\alpha$,17$\beta$-triol.

2. 7$\alpha$-methoxymethyl-17$\alpha$-ethynyl-$\Delta^4$-oestren-17$\beta$-ol.

3. 7$\alpha$-methoxymethyl-17$\alpha$-ethynyl-$\Delta^{1,3,5(10)}$-oestratriene-3,17$\beta$-diol.

4. 7$\alpha$-hydroxymethyl-17$\alpha$-ethynyl-$\Delta^{1,3,5(10)}$-oestratriene-3,17$\beta$-diol.

5. 7$\alpha$-methoxymethyl-$\Delta^{1,3,5(10)}$-oestratriene-3,16$\alpha$,17$\beta$-triol.

* * * * *